United States Patent [19]

Wagner

[11] 4,169,474

[45] Oct. 2, 1979

[54] LIQUID MEDICINE DISPENSERS WITH DOSE MECHANISMS FOR ORAL AND INJECTION THERAPY

[76] Inventor: Wolfgang Wagner, Klosterfelder Weg 29, 1 Berlin 27, Fed. Rep. of Germany

[21] Appl. No.: 813,494

[22] Filed: Jul. 7, 1977

Related U.S. Application Data

[63] Continuation of Ser. No. 639,685, Dec. 8, 1975, abandoned.

[30] Foreign Application Priority Data

Dec. 30, 1974 [GB] United Kingdom ............... 56007/74

[51] Int. Cl.² .............................................. A61J 1/00
[52] U.S. Cl. .............................. 128/272.3; 128/218 C
[58] Field of Search .......... 128/218 A, 218 C, 218 G, 128/213, 272.1, 272.3

[56] References Cited

U.S. PATENT DOCUMENTS

| | | | |
|---|---|---|---|
| 3,841,160 | 10/1974 | Iwao | 128/218 A X |
| 3,865,274 | 2/1975 | Genese et al. | 128/218 A X |
| 3,949,746 | 3/1976 | Wallach | 128/218 G |

*Primary Examiner*—John D. Yasko
*Attorney, Agent, or Firm*—Michael J. Striker

[57] ABSTRACT

It is intended, that the invention facilitate medicine therapy by providing the medicine supply containers directly with an adjustable dose mechanism, for which a medicine propulsion through a membrane, which is under pressure, is especially intended. For injection treatment, the possibility of a direct dubcutaneous injection through a cannula placed on a dose mechanism is created, to the extent that measures are taken to maintain sterility by special sealing devices (disinfection, suction, band movement etc). The filling of the syringes from a large supply in stationary injection use can generally be facilitated through the limitation of the movement of the syringe piston by dosage stops; the projection of sterility can be achieved with greater additions and costs (rinsing systeme etc). Finally, for oral use, rinsing-fluid and medicine containers are at least functionally connected with one another, so that counting of drops and rinsing glass are dispensed with. The smallest unit, the pressurized gas ampule, allows the use of different cannulas for individual doses.

1 Claim, 12 Drawing Figures

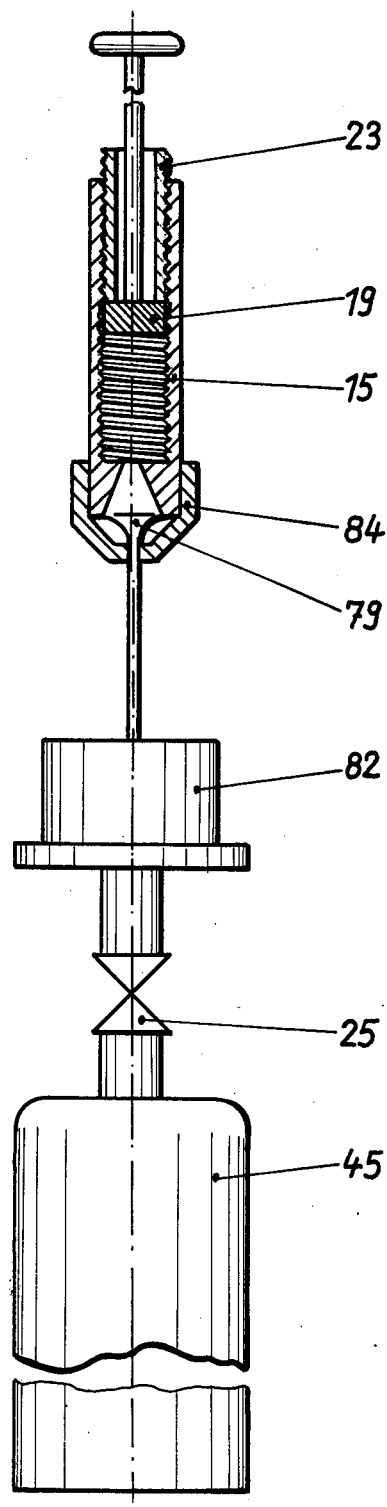

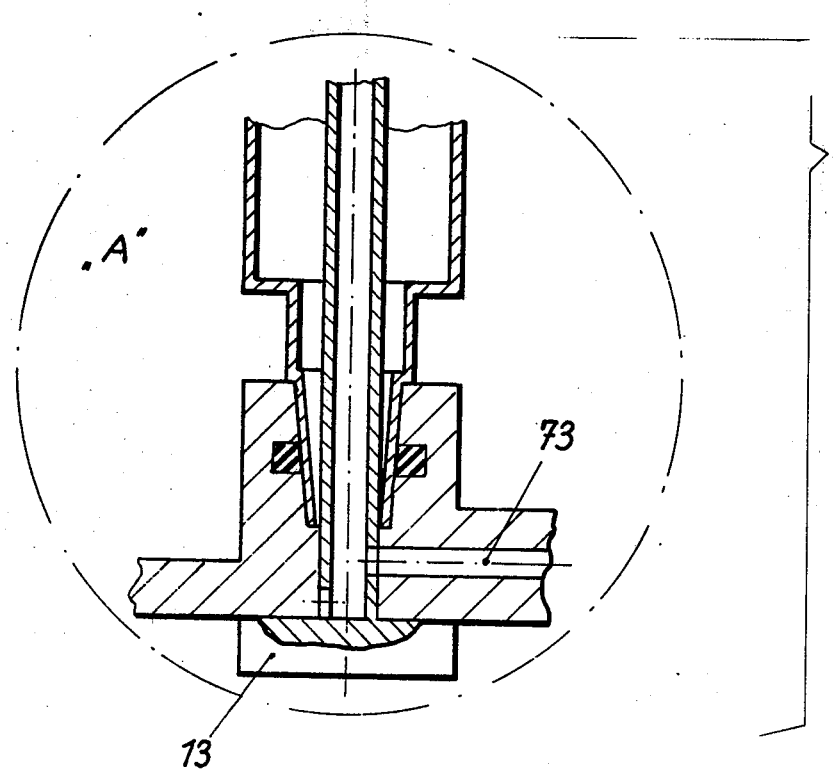

LIQUID MEDICINE DISPENSERS WITH DOSE MECHANISMS FOR ORAL AND INJECTION THERAPY

This is a continuation, of application Ser. No. 639,685, filed Dec. 8, 1975 now abandoned.

BRIEF SUMMARY OF THE INVENTION

This invention relates to medical technology especially to medical therapy. In the British application "Injection in Dose from Supply Containers" (N°4989/74) the possibility of a dosed injection by means of the formation of the supply containers as liquid dispensers for syringes was only briefly mentioned and did not include the possible use as drop dispensers, i.e. when used for oral dosage.

Liquid dispensers with fixed dosage are offered principally by the cosmetics industry. They are also used medically especially in connection with pressure storage bottles without separation of medicine from means of propulsion in spray containers for skin, mucous membranes or bronchi. $CF.Cl_3$.(Frigen 11,Hoechst),$CF.Cl_2$ and for mixture $CF_3.CFCl_2$ are known to technology or $CO_2$-gas in other use. In individual practices and clinics the troublesome cutting and breaking open of ampules and the filling syringes from ampules or from bottles sealed by stoppers after air insuflation as well as the counting of drops or measuring in measuring cups or spoons for oral dosage is generally in use. An apparatus for intracoutaneous injections with fixed does for one day is already known. The injection from a cannula which is directly connected to the supply container is expanded by the method of suction injection, an injection under skin which has been sucked in (Brit. 49990/74), especially for self-injection by diabetics. There the medicine container could be also a hose, especially for the intravenous injection.

The purpose of this invention is to facilitates the injection also from a larger storage bottle and also the oral therapy. The principles for dosing are carried out by a Example with air chamber for ventilation of a medical bottle inside of a separating membrane, expanded to dose mechanisms with pressure storage containers in which the medicine is separated from the pressure gas or liquid by membrane, folded bellows or piston or a combination of them. The amount of medicine can be better determined and the quality of this preserved (from contact with the membrane) when the medicine is separated from the folded bellows by an additional glass or plastic piston, which must seal out all liquid but not gas. A dose piston, which is to be used from the front or the other side, while space is saved within the mechanism by the use of flexible service element (pulling core), can be easily mounted on a pressure storage bottle. But the presented dose mechanism with cord required a movement for the renewal of tension before each use. Beside that the sealing off of the cord inlet in the dose cylinder was a rather critical point with regard to the goal of the preservation of cleanliness and presented the danger of allowing the mixture of traces of the disinfection material, which used for sealing the cord, to enter the medicine as a result of cord movement. The difficulties are solved here by the use of an elastic cone, which can be made for example of rubber or silicone, to the point of which the dose piston is attached. The cord, which leads to the point of the cone or the dose piston, is kept separated from the medicine in a passage in the cone, which leads towards the outside. The medicine inflow is brought about from the front (not far from the excentrically placed medicine outlet) against the pressure of a spring behind the dose piston or outside. The movement of the dose piston is limited by the pretermined length of the cord. The medicine is prevented from flowing out by a valve, which is opened by lever movement, by cannula pressure on a checkvalve, or directly by the suction of a mechanism for suction injection. Such a tension activated valve however also prevents accidental activation when used in other forms, e.g. for oral use. The combination of two dose pistons or more and the exchangeability of the medicine containers permits any desired combination of medicine dosages or types. A valve ring can be directly steered over grooves (p.e. of a injection apparatus) and can be activated at the time as the cannula fixing. For private practices and clinics a syringe filling from larger medical bottles is shown. The problems of dosing were solved by dose mechanisms for a fixed dosage in the neck of the medicine bottle with pressure propulsion or in the bottom of the bottle by hand or by the principle of the direct blocking of piston in the syringe, as well inside of them as on an outer barrier or of a blocking of the cylinder movement, while the piston is attached in fixed position, when amounts to the thame thing, or of a Blocking inside of an dose case or injection apparatus. An essential prerequisite for use of larger supply containers, namely a reproduction for germ and contamination of the medicine supply hindering mechanisms, and further practical arrangements of several supply containers in a block are emphazed. A supplement is the broadening of the use to dry substances, which can be dissolved in a case. A mechanical attachment within the dispenser or in a fixed connection to them, which allows a better mixing of powder and solution, especially by use of a piston or by making the mixing space smaller, while the dissolved medicine is emptied by an extra force which is thus produced and subsequently takes effect, presents advantages, for example, for the use of G-penicillin, especially for rheumatic fever. A further simplification of the process of maintaining sterility results from the use of fluids, especially germicidal, in the space around the cannula or cannula attachment, especially when the latter can be sunk in the fluid, either before or after use. As to the form of filler neck, one of the most important points are to keep the amount of air which is over the medicine supply after use as small as possible, to guarantee on air-tight seal, to remove any germs which have been drawn in, whether this had come about through the movement of bands, through suction between syringe and the funnel of the filler neck or the liquid stream likewise of a medicine bottle with its opening facing downwards, a position which especially for oral use seems to be useful in protecting from dust and in facilitating use, since one extra movement is thereby eliminated. The germicidal, oligodynamic effect of a metal should also be considered, and especially the effect of an automatic, self-closing, mechanical seal, in order to shorten the period of air contact, and finally the cooling or heating of the cannula or arround the cannula attachment. Before this happened it may be necessary to clean the cannula and to make it empty of the medicine with the helb of a water or gas stream which comes either from the driving gas supply or the cleansing water container.

In order to prevent the covering fluid or mass from getting in to the cannula or cannula attachment, devices are necessary, which cause the covering fluid to withdrawn from the medicine outlet opening bevore use of the apparatus, or which cover the medicine outlet opening by closing the cannula attachment nozzle (filler neck), either from within or without, or which allow an almost complete emptying of the cannula attachment mozzle of medicine by the use of a rinsing stream, of liquid or especialy of gas, following the injection, and further permit the use of a cleansing stream, when the cannula attachment nozzle penetrate the covering fluid (mass). Instead of the covering fluid, a viscous mass can be more efficiently used, while a disinfectant can kill off any germs which have penetrated the area, while the mass flows in. Other wise: Germs which appear on the surface of the mass are either destroyed or at least prevented from multiplaying by the shifting or mixing which brings them in to the middle of the mass. Disinfectant in connection with a silicon or plastic material has a similiar germicid effect as the oligodynamic effect of metalic surfaces. A higher adhesion, viscosity or thixotropy renders more difficult the runing away of the covering fluid after use. The cannula attachment may be retired for cleansing in to the fluid stream. In private practise and clinics the use of cleansing fluid, especially distilled water, for cleansing a medicine within the dose mechanism, especially through automatic periodic rinsing, avoids the builsup threat to proper valve functioning; the flowing off of the cleansing fluid through the lid facilitates the complete rinsing away of germs; such an apparatus also saves one from having to put dose mechanisms in the medicine supply bottles (what means the use of disposible dose mechanisms) and even permits a change in the medicine, which results in a lessing of the costs.

In FIG. 1 the dose mechanism is replaced by a blocking (64) of the piston rod of the syringe which is placed on the funnel (45). A blocking rod with a clamo (65) is raised up after the dosage together with the syringe by the sored up pressure of a spring, so that the syringe cone is drawn out of the syringe funnel.

In FIG. 1a the blocking rod is, for example, attached to and removable from the pressure storage bottle. The blocking of the piston rod can be pulled back against a spring, and at the same time adjusted along a dose scale (17). Pegs can be inserted in pretermined places.

In FIG. 1b the variation is in the connection with the medicine bottle, which is inserted into a joint. This allows at least two blocking rods of different heights to be swung in.

In FIG. 1c, the syringe which is to be filled is shoved into a cylinder, inside of which a screw (66) with a dosescale and spring mechanism (17), as desdribed in FIG. 2, allows an exact determination of the dosage.

The use of the principle within a injection apparatus is shown in FIG. 1d, in the example of a mechanism for subcutaneous, single-suction injection. The syringe cylinder is pushed into the suction cylinder up to the stop (67)., the sealing piston rod (68) is adjusted in height according to the scale and the spring mechanism (dosescale, 17) after the snaping in of the dose nut (69) in the catch (70). After the syringe cone has been led into the syringe funnel of a pressure storage bottle, as well as after the activation of the check valve, the syringe piston is raised to the position which has been selected. By pulling of the handle (71) the stop (67) and the catch (70) disengaged, and the syringe can be raised by means of the leading clamp (72) on the rod (68) until the dose nut snaps into the groove and snap (38), after the cannula has been put on. After the freeing of a spring which has up til that point been under tension, a piston movement creates suction, which sucks on the skin. The piston movement drives a cannula through the skin ans forces the medicine out of the syringe.

Figure 1:
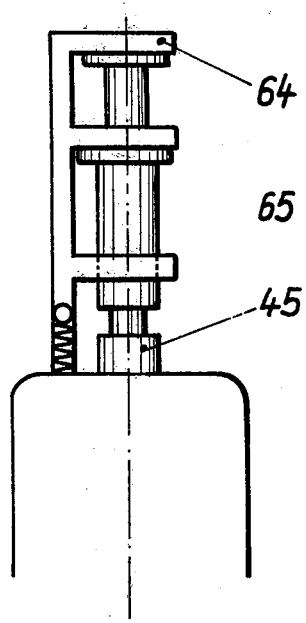
FIG. 1e shows a dosage in which the upwards movement of the piston is prevented by an adjustable stop inside of the syringe.
FIG. 1f shows a syringe whose piston is stopped by the snapping in of a peg, driven by a spring, into a hole in the piston shaft. The blocking (64) of the peg can be removed by pulling the peg.
FIG. 1g shows a blocking rod with a syringe clamp, which is placed on the syringe cylinder, and determines either rigidly or adjustable the distance between the end of the piston and the end of the cylinder.
Figure 1A:
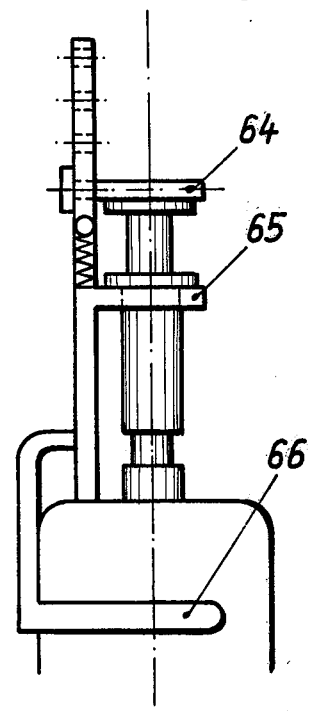
Figure 1B:
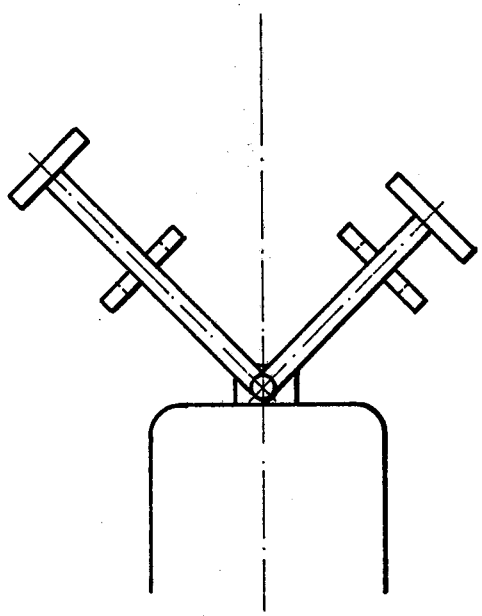
Figure 1C:
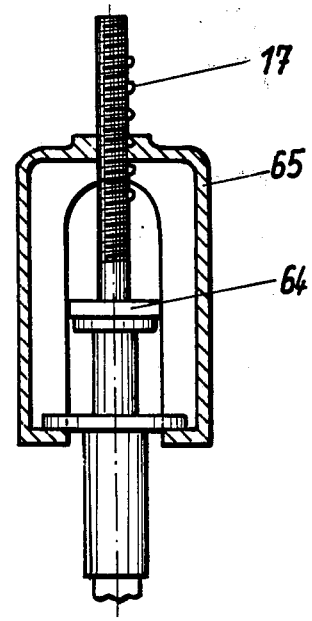
Figure 1D:
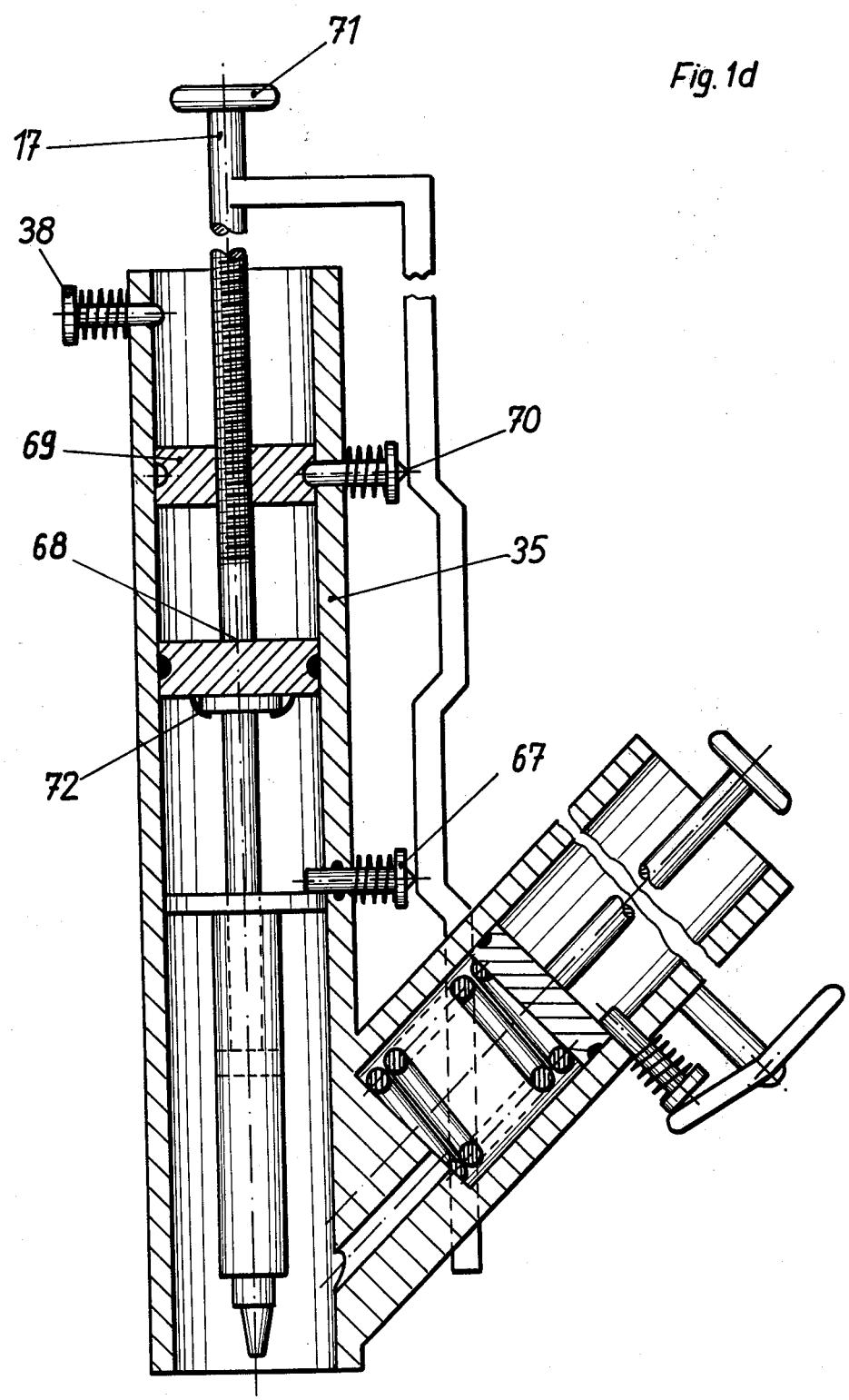
Figure 1F:
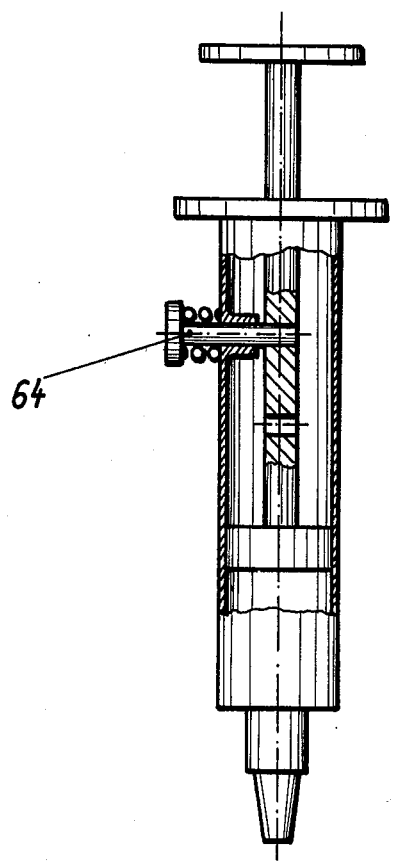
Figure 1G:
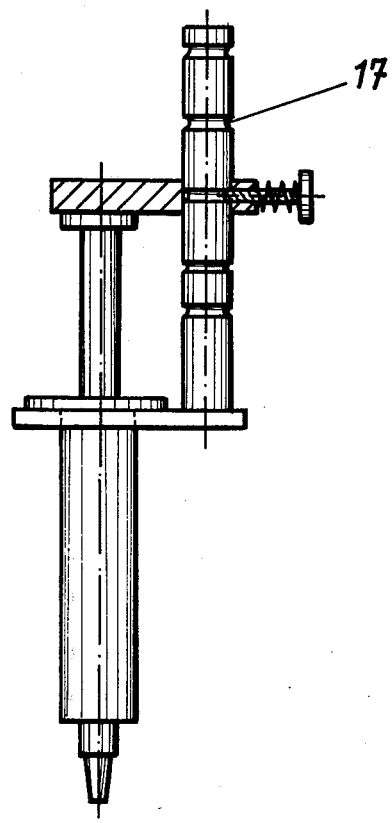
Figure 1H:
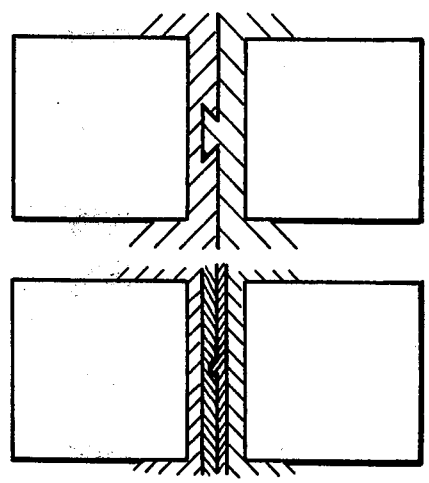

FIG. 1h shows an example of the connection of several pressure storage bottles, which have a square form and a guide groove and channel on the proper places on the sides of the bottles, so that they can be fitted into another and formed into a block. In variation of Detail the bottles are connected by plastic rings. By means of slot between the sides of the bottles, the block of bottles can fitted onto a cooling rod, which is connected to a cooling mechanism with a thermostat both under the table.

In FIG. 1i, the connection of a double bottle with separate medicine supplies and one filler neck is shown. The latter is placed over a check valve (30). The function of which is determined by the length of the filling tube (5). When not in use, the filling tube is protected by a cushioning membrane. If the filling tube is brought out to its full length, its side opening (82) comes together with the supply tube (73). After the dose mechanism of the second medicine bottle (part), is activated by the handle, the second medicine can flow in and rinses the filtube nearly of the filler neck free of the first medicine.

Figure 1J:
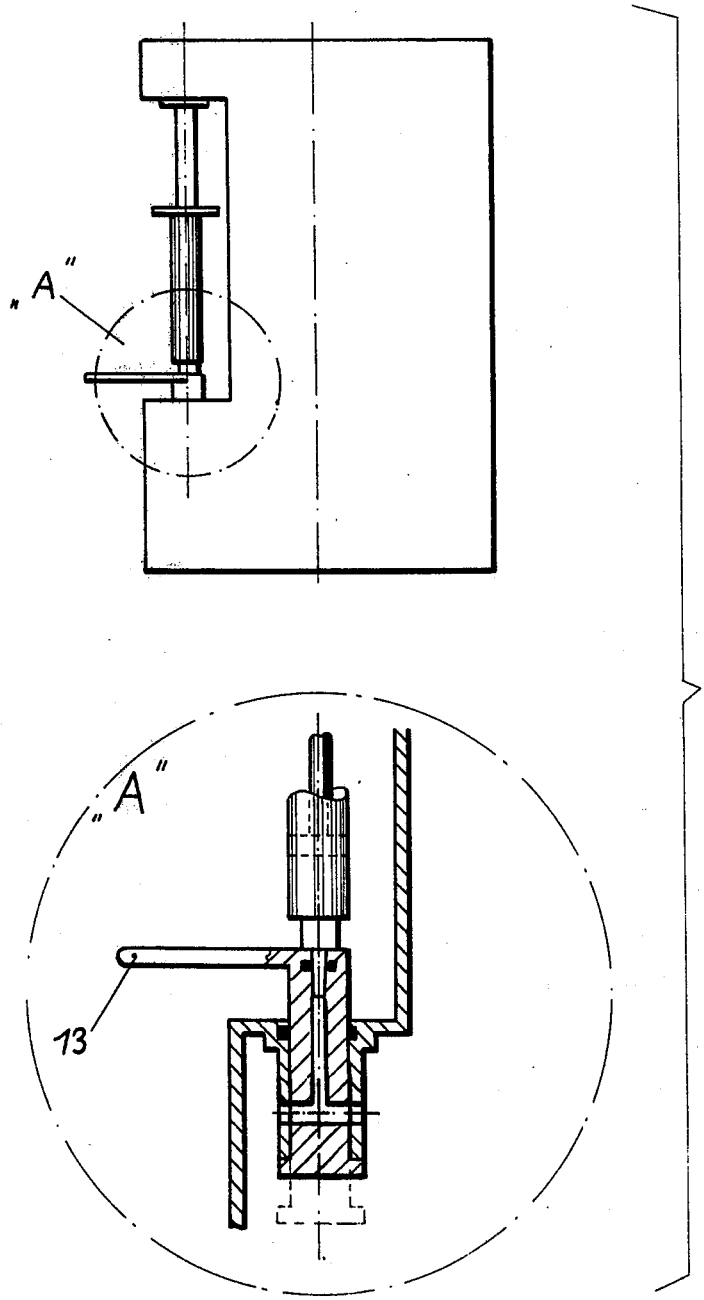

In FIG. 1j, there is a dose niche on the edge of the medicine bottle. The syringe is put into the valve case (13) after te sealing lid has been lifted. Then the syringe and the valve case are pulled up, and there by the correspondingly formed valve is opened. After the dosage the valve ease is pressed down with a finger, and the removal of the syringe is made possible.

Figure 1K:
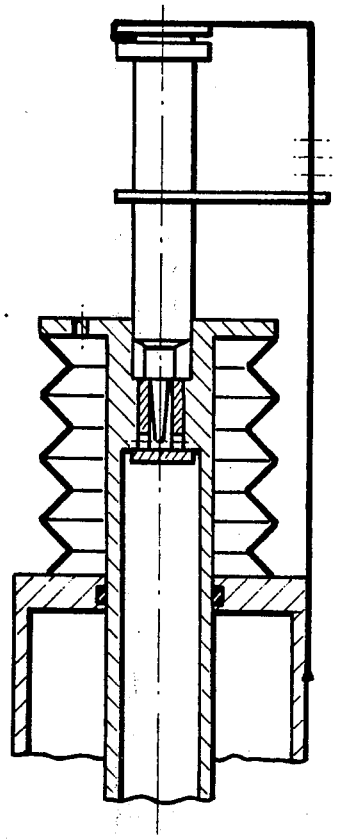

FIG. 1k shows a solution, in which a holding clamp for the syringe piston is attached on the medicine bottle, otherwise the syringe cylinder is moved to a stop for the dosing variable or not whilst the checkvalve for medicine outlet is activated. After the filled syringe is removed, the cushioning folded bellows is raising again.

I claim:

1. A container, particularly for storing liquid medicine, comprising a casing having walls bounding an interior of the container for keeping the medicine, said casing having one openable end for releasing the medicine therethrough when this end is open and another end spaced from said one end; means operative for urging the medicine out of the casing through said one end thereof when said one end is open; means for sealingly closing said casing so as to prevent any undesired contamination of the medicine inside the casing and including first means selectively movable from a first position in which it sealingly closes said one end of said casing into a second position it which it opens said one end of the casing for permitting a predetermined amount of the medicine to leave the casing, and from said second position into said first position when the predetermined amount of the medicine has been released from said casing; and external abutments for varying operation of said urging means to thereby vary the amount of the medicine urged out of the casing.

* * * * *